(12) United States Patent
Eynon et al.

(10) Patent No.: US 7,519,519 B1
(45) Date of Patent: Apr. 14, 2009

(54) SIGNATURE PROJECTION SCORE

(75) Inventors: Barrett P. Eynon, Menlo Park, CA (US); Georges Natsoulis, Kensington, CA (US); Kurt Jarnigan, San Meteo, CA (US)

(73) Assignee: Entelos, Inc., Foster City, CA (US)

( * ) Notice: Subject to any disclaimer, the term of this patent is extended or adjusted under 35 U.S.C. 154(b) by 42 days.

(21) Appl. No.: 10/741,506

(22) Filed: Dec. 18, 2003

Related U.S. Application Data

(60) Provisional application No. 60/435,883, filed on Dec. 20, 2002.

(51) Int. Cl.
G06F 17/10 (2006.01)
G06F 7/60 (2006.01)

(52) U.S. Cl. .............................. 703/2; 702/19; 702/23; 435/6; 436/63

(58) Field of Classification Search ........................ None
See application file for complete search history.

(56) References Cited

U.S. PATENT DOCUMENTS

| | | | |
|---|---|---|---|
| 5,523,208 A | 6/1996 | Kohler et al. | |
| 5,706,498 A | 1/1998 | Fujiyama et al. | |
| 5,953,727 A | 9/1999 | Maslyn et al. | |
| 5,966,712 A | 10/1999 | Sabatini et al. | |
| 6,040,138 A | 3/2000 | Lockhart et al. | |
| 6,134,344 A | 10/2000 | Burges | |
| 6,203,987 B1 | 3/2001 | Friend et al. | |
| 6,427,141 B1 | 7/2002 | Barnhill | |
| 7,054,755 B2 * | 5/2006 | O'Reilly et al. | ........ 702/19 |
| 2002/0042681 A1 | 4/2002 | Califano et al. | |
| 2002/0095260 A1 | 7/2002 | Huyn | |
| 2002/0111742 A1 | 8/2002 | Rocke et al. | |
| 2002/0119462 A1 | 8/2002 | Mendrick et al. | |
| 2002/0174096 A1 | 11/2002 | O'Reilly | |
| 2004/0259764 A1 * | 12/2004 | Tugendreich et al. | ....... 514/1 |

FOREIGN PATENT DOCUMENTS

| | | |
|---|---|---|
| EP | 1037158 | 9/2000 |
| WO | WO00/37685 | 6/2000 |
| WO | WO00/63435 | 10/2000 |
| WO | WO00/65523 | 11/2000 |
| WO | WO00/70528 | 11/2000 |
| WO | WO01/25473 | 4/2001 |
| WO | WO 0231704 A1 | 4/2002 |

OTHER PUBLICATIONS

T.R. Golub et. al., "Molecular Classification of cancer: Class Discovery and Class Prediction by Gene Expression Monitoring", *Science* v. 286 (1999), 531-37.
D.J. Lockhard, et. al., "Expression Monitoring by Hybridization to High-Density Oligonucleotide Arrays", *Nature Biotechnology* v. 14 (1996), 1675-80.
G. McGall, et. al.,"Light-Directed Synthesis of High-Density Oligonucleotide Arrays Using Semiconductor Photoresists", *Proc Natl Acad Sci USA* v. 96 (1996), 13555-60.
Poli, "The Role of C/EBP Isoforms in the Control of Inflammatory and Native Immunity Functions", *J Biol Chem* v. 278 (1998), 29279-82.

* cited by examiner

*Primary Examiner*—Carolyn L. Smith

(57) ABSTRACT

Disclosed is a method for predicting the biological activity of a compound by the similarity of its drug signature score to the scores of a plurality of known drug signatures.

19 Claims, 2 Drawing Sheets

SIGNATURE PROJECTION SCORE

RELATED APPLICATIONS

This application claims priority from U.S. Provisional Application No. 60/435,883 filed Dec. 20, 2002, which is hereby incorporated by reference in its entirety.

FIELD OF THE INVENTION

This invention relates to the fields of genomics, chemistry, and drug discovery. More particularly, the invention relates to methods and systems for grouping and classifying compounds by their ability to cause similar biological effects ("drug signatures"), and methods and systems for predicting the accuracy and quality of such drug signatures.

BACKGROUND OF THE INVENTION

During the course of drug discovery, optimization and development researchers are faced with many important decisions. These decisions frequently determine the success or failure of the drug discovery and optimization program, or at the very least directly affect the number and duration of optimization cycles necessary to develop a treatment for the target disease.

Deciding which lead series of chemical molecules to optimize is of critical importance, complicated by the fact that modern high throughput screening often places 5-10 such options before the discovery team. Decisions are made within a lead series about which molecules deserve further optimization, and about which molecules receive detailed in vivo evaluation. Several of these decisions commit dozens of research workers to experimental programs that may last 1-3 years, so any suboptimal decision can easily result in substantial financial and opportunity costs. Further, in many cases patents will have already been filed and/or granted covering the molecules about which the decisions are being made, and poor decisions can delay a drug's arrival on the market by several years, and thus the length of the effective patent protection for the drug. Thus, an erroneous selection of a compound for final optimization or for detailed in vivo examination can be a very costly error. These key decisions are significant and deserve to be supported with detailed, accurate, and topical experimental findings directed toward fully understanding a candidate's toxicology and mechanism of action.

In current practice many of these critical decisions are made based on an experienced drug developer's best judgment of likely toxicological and off-target effect profiles. This judgment and intuition can be improved and supplemented by chemogenomic annotation of the candidate and comparison of the candidate's profile with a large database of chemogenomic annotations.

"Chemogenomic annotation" is the process of determining the transcriptional and pharmacological response of one or more genes to exposure to a particular chemical, and defining and interpreting such responses in terms of the classes of chemicals for which they interact. A comprehensive library of chemogenomic annotations would enable one to design and optimize new pharmaceutical lead compounds based on the probable transcriptional and biomolecular profile of a hypothetical compound with certain characteristics. Additionally, one can use chemogenomic annotations to determine relationships between genes (for example, as members of a signaling pathway or protein-protein interaction pair), and to aid in determining the causes of side effects and the like. Finally, presenting the drug design researcher with a body of chemogenomic annotation information will generate research hypotheses that will stimulate follow-on experiments and may stimulate changes in the researcher's drug design plan, including development or inclusion of additional counter screens, or may stimulate the selection and elaboration of an alternate lead series, which is revealed by the chemogenomic library to have preferable characteristics.

Several genomic database models have been disclosed. Sabatini et al., U.S. Pat. No. 5,966,712 disclosed a database and system for storing, comparing and analyzing genomic data. Maslyn et al., U.S. Pat. No. 5,953,727 disclosed a relational database for storing genomic data. Kohler et al., U.S. Pat. No. 5,523,208 disclosed a database and method for comparing polynucleotide sequences and the predicted functions of their encoded proteins. Fujiyama et al., U.S. Pat. No. 5,706,498 disclosed a database and retrieval system, for identifying genes of similar sequence.

Sabry et al., WO00/70528 disclosed methods for analyzing compounds for drug discovery using a cellular informatics database. The system photographs cells that have been manipulated or exposed to test compounds, converting the resulting data into a database. Sabry further describes constructing a database of "cellular fingerprints" comprising descriptors of cell-compound interactions, where the descriptors are a collection of identified data/phenotype variations that characterize the interaction with compounds of known action, constructing a phylogenetic tree from the descriptors, and determining the statistical significance of each descriptor. The descriptor for a new compound can be compared to the phylogenetic tree to determine its most likely mode of action.

Winslow et al., WO00/65523, disclosed a system comprising a database containing biological information which is used to generate a data structure having at least one associated attribute, a user interface, an equation generation engine operative to generate at least one mathematical equation from at least one hierarchical description, and a computational engine operative on the mathematical equation to model dynamic subcellular and cellular behavior. The system is intended to access and tabulate genetic information contained within proprietary and nonproprietary databases, combine that data with functional information regarding the biochemical and biophysical role of gene products, and based on this information formulate, solve and analyze computational models of genetic, biochemical and biophysical processes within cells.

Gould-Rothberg et al., WO00/63435, disclosed a method for identifying hepatotoxic agents by exposing a test cell population comprising a cell capable of expressing one or more nucleic acids sequences responsive to troglitazone (an anti-diabetes drug discovered to cause liver damage in some patients during phase III trials), contacting the test cell population with the test agent and comparing the expression of the nucleic acids sequences in a reference cell population. An alteration in expression of the nucleic acids sequences in the test cell population compared to the expression of the gene in the reference cell population indicates that the agent is hepatotoxic. Gould-Rothberg et al., WO00/37685, disclosed a method for identifying psychoactive agents that lack motor involvement, by identifying genes transcriptionally activated in rat brain striatum in response to haloperidol. Compounds that do not induce these genes are believed to not result in side effects.

Friend et al., U.S. Pat. No. 6,203,987, discloses a method for comparing array profiles by grouping genes into co-regulated sets ("genesets"). Friend et al. disclose an embodiment in which the expression profile obtained in response to a drug is projected into a geneset, and compared with other genesets to determine the biological pathways affected by the drug. In another embodiment, the projected profiles of drug candidates are compared with the profiles of known drugs to identify possible replacements for existing drugs.

Tamayo et al., EP 1037158, disclosed a method for organizing genomic data using Self Organizing Maps to cluster gene expression data into similar sets. The method was assumed to identify drug targets, by identifying which move from their expression clusters after a test cell is exposed to a given compound.

Tryon et al., WO01/25473, disclosed a method for constructing expression profiles of genes in response to a drug. In this method, a number of genes are selected on the basis of their expected interaction with the drug or condition to be examined, and their expression in cell culture is measured in response to administration of the drug.

SUMMARY OF THE INVENTION

Figure 1:
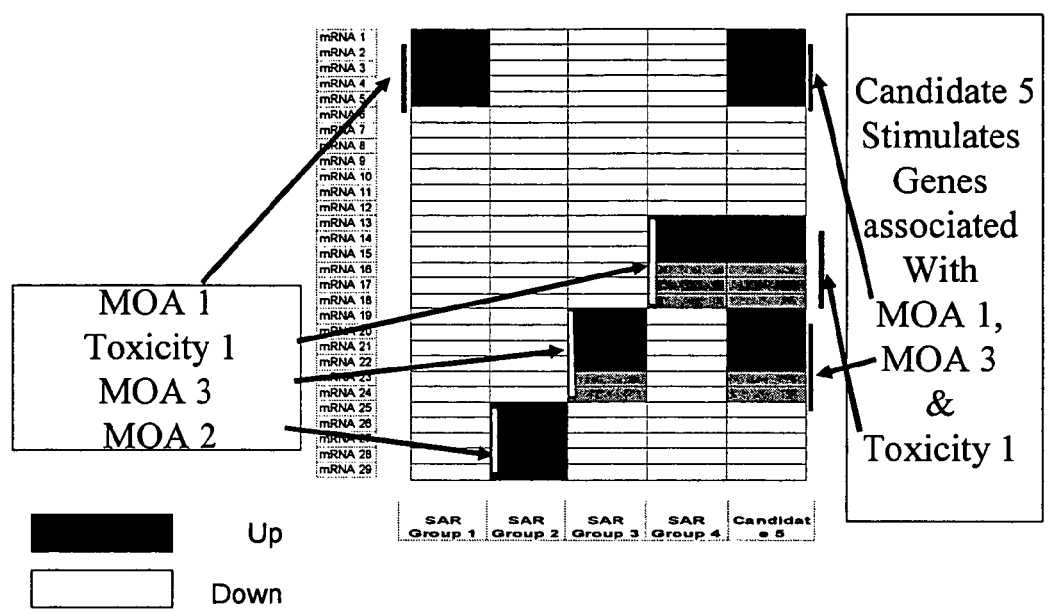
FIG. 1 depicts a hypothetical display of expression data that illustrates how signatures can facilitate data interpretation.

A central aspect of the present invention is the design of a technique for determining how similar the drug signature of a drug or compound is, compared to the signature of known drugs and/or activities. The resulting score can be used to predict how closely the biological activity of the test drug or compound will resemble the biological activity of the compounds from which the closest drug signature is derived.

One aspect of the invention is a method for testing the propensity of a test compound to demonstrate a known biological activity, comprising: contacting a test subject with an effective amount of a test compound, measuring the genomic response of the test subject, and comparing the genomic response to a selected Drug Signature to determine its Signature Projection Score. Preferably, the test compound signature is compared to a plurality of Drug Signatures, and a Signature Projection Score is calculated for each pair-wise combination: the combinations are then ranked by score in order to determine which Drug Signature most closely resembles the test compound signature. In one aspect, the database comprise at least 10 drug signatures, preferably at least 25 drug signatures, more preferably at least 100 drug signatures, and even more preferably in the range of 100 to 10,000 drug signatures. In another aspect, the biological activities of the test compound are therapeutic and/or toxicological activities.

DETAILED DESCRIPTION

Definitions

The term "test compound" refers in general to a compound to which a test subject is exposed. Typical test compounds will be small organic molecules, typically drugs and/or prospective pharmaceutical lead compounds, but can include proteins, peptides, polynucleotides, heterologous genes (in expression systems), plasmids, polynucleotide analogs, peptide analogs, lipids, carbohydrates, viruses, phage, parasites, and the like.

The term "control compound" refers to a compound that is not known to share any biological activity with a test compound, which is used in the practice of the invention to contrast "active" (test) and "inactive" (control) compounds during the derivation of Group Signatures and Drug Signatures. Typical control compounds include, without limitation, drugs used to treat disorders distinct from the test compound indications, vehicles, inactivated versions of the test agent, known inert compounds, and the like.

The term "biological activity" as used herein refers to the ability of a test compound to affect a biological system, for example to modulate the effect of an enzyme, block a receptor, stimulate a receptor, alter the expression of one or more genes, and the like. Test compounds have similar or identical biological activity when they have similar or identical effects on an organism in vivo or on cells or proteins in vitro. For example, fenofibrate, clofibrate, and gemfibrozil have similar biological activities because all three are prescribed for hyperlipoproteinemia or interact with similar or identical molecular targets. Similarly, aspirin, ibuprofen, and naproxen all have similar activities as all three are known to be non-steroidal anti-inflammatory compounds or interact with similar or identical molecular targets. The terms "primary bioactivity" and "primary biological activity" refer to the most pronounced or intended effect of the compound. For example, the primary bioactivity of an ACE inhibitor is the inhibition of angiotensin-converting enzyme (and the concomitant reduction of blood pressure), regardless of secondary bioactivities or side effects.

The term "test subject" refers to a biological organism, cell, tissue, or a model of a biological system capable of reacting to the presence of a test compound, typically a live animal, eukaryotic cell or tissue sample, or a prokaryotic organism.

The term "expression response" refers to the change in expression level (or could note a lack of change) of a gene in response to administration of a test compound or control compound (or other test or control condition). The expression level can be measured indirectly, for example by quantifying the amount of protein encoded by the gene that is produced using proteomic techniques, or can be measured directly as the change in mRNA transcription, or by any other quantitative means of measuring gene activation. The expression response can be weighted or scaled as necessary to normalize data, and can be, reported as the absolute increase or decrease in expression (or transcription), the relative change (for example, the percentage change), the logarithm of the relative change, the degree of change above a threshold level, and the like.

The term "expression dataset" as used herein refers to data indicating the identity of genes affected by administration of the test or control compound, and the change in expression that resulted. The expression dataset typically contains a subset of genes, preferably the subset of genes that displayed the most compound-specific changes in expression response.

The terms "PCA" and "principal component analysis" refer to mathematical methods for transforming a number of correlated variables into a number of uncorrelated (independent) variables called principal components. The first principal component accounts for as much of the variability in the data as possible, and each succeeding component accounts for as much of the remaining variability as possible. "PCA" as used herein further includes variations of principal component analysis such as kernel PCA and the like.

The term "discrimination metric" refers to a method or algorithm for distinguishing the expression data in response to test compounds from the expression data in response to other compounds. The method can involve selecting genes on the basis of the eigenvalues for the genes from the PCA output (selecting the principal component axis that separates the test compounds from the control compounds), or can include mathematical analysis to determine which gene or combination of genes best discriminates between the test and control compounds, for example using Golub's distinction metric, Student's t-test, linear discriminant analysis methods like support vector machines, neural networks, decision trees or Bayesian methods or other appropriate methods. Those skilled in the art will be aware of these methods and could refer to "The Elements of Statistical Learning: Data Mining, Inference and Prediction", T. Hastie, R. Tibshirani, J. Friedman, Springer-Verlag, New York, 2001 to find descriptions and implementation details.

The term "Group Signature" as used herein refers to a data structure comprising a group identifier and one or more gene identifiers. The group identifier indicates a family of compounds having similar activity (for example, "fibrates"), or groups of compound treatments that produced a defined phenotype (hepatocellular damage, for example), or can directly indicate the activity (for example, PPARα inhibition). It is often simply the "name" of the group. The group identifier can further indicate the identity of compounds known to belong to the group. Gene identifiers indicate genes whose expression has been modified (induced, repressed or unchanged) by administration of a compound belonging to the group, and which are so characteristic of the group, or so distinctive, that modulation of the expression of these genes according to the signature is sufficient to distinguish the compound administered as belonging to the Group (rather than to another Group, or wholly lacking known activity). The gene identifiers can identify genes by sequence, name, reference to an accession number, reference to a clone or position within a DNA array, and the like. Paired with each gene identifier can be a term that further comprises the direction and degree of expression modulation and its direction of contribution to the discriminator, in absolute or relative terms. For example, a gene identifier can include the requirement that expression increase by at least 100%, or that expression increase by between 100% and 500%. The gene identifier can further include time restrictions: for example, a Group Signature can require that gene "X" be upregulated by at least 250% within 8 hours of administration, or at not less than 4 hours but no more than 16 hours, or the like. The Group Signature typically comprises about 2 to about 50 gene identifiers of varying degrees of specificity, from which sub-sets of varying specificity can be derived; however at other times signatures of length 100, 500 or even all genes present in the detection array may be desirable. For example, the most specific signature for one group may comprise 20 gene identifiers: this signature contains a plurality of sub-signatures having similar (or somewhat less) specificity derived by omitting one or more of the gene identifiers. The Group Signature can further comprise pharmacological data or clinical chemistry or clinical observations or clinical histopathology findings, for example indicating the bioactivity observed for compounds in the group against a panel of standard assays. Pharmacological, clinical chemistry, clinical observations or clinical histopathology data can be used to identify the potential members of a Group prior to genomic experiments, particularly where a number of drug candidates are to be screened. Bioactivity data is particularly useful for distinguishing between compounds having unrelated structures, but which induce similar genomic expression patterns. The data structure can be stored physically or electronically, for example within a database on a computer-readable medium. Alternatively, the data structure can be embodied in an array in full or in part, such as a polynucleotide probe array having a separate region of probes specific for each Group Signature. Finally, although a signature may have been developed in the context of one or more species employed as experimental hosts, the genes identified in a signature are considered to also include their homologs and orthologs (genes found in another species, preferably mammalian, but behaving similarly to or having a similar response as the genes identified in a signature).

The term "Group Signature database" refers to a collection of data comprising a plurality of Group Signatures. A number of formats exist for storing data sets and simultaneously associating related attributes, including without limitation, tabular, relational, and dimensional. The tabular format is most familiar, for example spreadsheets such as Microsoft Excel® and Corel Quattro Pro® spreadsheets. In this format, association of data points with related attributes occurs by entering a data point and attributes related thereto in a unique row. Relational databases typically support a set of operations defined by relational algebra. Such databases typically include tables composed of columns and rows for the data included in the database. Each table in the database has a primary key, which can be any column or set of columns, the values for which uniquely identify the rows in the table. The tables in a relational database can also include a foreign key that is a column or set of columns, the values of which match the primary key values of another table. Typically, relational databases support a set of operations (for example, select, join, combine) that form the basis of the relational algebra governing relations within the database. Suitable relational databases include, without limitation, Oracle® (Oracle Inc., Redwood Shores, Calif.) and Sybase® (Sybase Systems, Emeryville, Calif.) databases.

The term "Drug Signature" as used herein refers to a data structure similar to the Group Signature, but specific to a single compound (or a plurality of essentially identical compounds, such as salts or esters of the same compound). The gene identifiers of a Drug Signature are selected to distinguish the selected compound from other compounds with which it shares activity(ies): Drug Signatures distinguish between members of a Group Signature, and could also distinguish between the drug compound and unrelated compounds.

The term "gene expression profile" refers to a representation of the expression level of a plurality of genes in response to a selected expression condition (for example, incubation in the presence of a standard compound or test compound). Gene expression profiles can be expressed in terms of an absolute quantity of mRNA transcribed for each gene, as a ratio of mRNA transcribed in a test subject as compared with a control test subject, and the like. As used herein, a "standard" gene expression profile(s) refers to a profile already present in the primary database (for example, a profile obtained by incubation of a test subject with a standard compound, such as a drug of known activity), while a "test" gene expression profile refers to a profile generated under the conditions being investigated. The term "modulated" refers to an alteration in the expression level (induction or repression) to a measurable or detectable (and statistically significant) degree, as compared to a pre-established standard(s) (for example, the expression level of a selected tissue or cell type at a selected phase under selected conditions).

The term "correlation information" as used herein refers to information related to a set of results. For example, correlation information for a profile result can comprise a list of similar profiles (profiles in which a plurality of the same genes are modulated to a similar degree, or in which related genes are modulated to a similar degree), a list of compounds that produce similar profiles, a list of the genes modulated in said profile, a list of the diseases and/or disorders in which a plurality of the same genes are modulated in a similar fashion, and the like. Correlation information for a compound-based inquiry can comprise a list of compounds having similar physical and chemical properties, compounds having similar shapes, compounds having similar biological activities, compounds having similar clinical chemistry, blood cell type, histopathology or clinical observations, or compounds that produce similar expression array profiles, and the like. Correlation information for a gene- or protein-based inquiry can comprise a list of genes or proteins having sequence similarity (at either nucleotide or amino acid level), genes or proteins having similar known functions or activities, genes or proteins subject to modulation or control by the same compounds, genes or proteins that belong to the same or similar metabolic or signaling pathway, and the like. In general, correlation information is presented to assist a user in drawing parallels between diverse sets of data, enabling the user to create new hypotheses regarding gene and/or protein function, compound utility, compound side effects, compound toxicity, and the like. Product correlation information assists the user with locating products that enable the user to test such hypotheses.

"Similar", as used herein, refers to a degree of difference between two quantities that is within a preselected threshold. For example, two genes can be considered "similar" if they exhibit sequence identity of more than a given threshold, such as for example 20%. A number of methods and systems for evaluating the degree of similarity of polynucleotide sequences are publicly available, for example BLAST, FASTA, and the like. See also Maslyn et al. and Fujimiya et al., supra, incorporated herein by reference. The similarity of two profiles can be defined in a number of different ways, for example in terms of the number of identical genes affected, the degree to which each gene is affected, and the like. Several different measures of similarity, or methods of scoring similarity, can be made available to the user: for example, one measure of similarity considers each gene that is induced (or repressed) past a threshold level, and increases the score for each gene in which both profiles indicate induction (or repression) of that gene. For example, if $g_x$ is gene "x", and $P_{Ex}$ is the expression level of $g_x$ in an experimental profile, $p_{Sx}$ is the expression level of $g_x$ in a standard profiles, and $p_T$ is a pre-determined threshold level, we can define function H for any experimental ("E") and standard ("S") profile pair as $H_{E,S}=1$ when both $p_{Ex}$ and $p_{Sx} \geq p_T$, and $H_{E,S}=0$ when either $p_{Ex}$ or $p_{Sx} < p_T$. Then, a simple similarity score can be defined as $N=\Sigma_x H_x$. This similarity score counts only the genes that are similarly induced in both profiles. A more informative score can be calculated as $N'=\Sigma_x (H_x)^* |p_{Ex}-p_{Sx}|^* (p_{Ex}^* p_{Sx})^{-1/2}$, which also takes into consideration the difference in expression level between the experimental and standard profiles, for each gene induced above the threshold level. Other statistical methods are also applicable.

The term "probe" as used herein refers to a polynucleotide, for example an oligonucleotide having at least 5 bases, a longer polynucleotide of 30-1,000 bases or more, and the like, whether occurring naturally (as in a purified restriction digest) or produced synthetically, recombinantly or by PCR amplification, that is capable of hybridizing to another polynucleotide of interest. A probe can be single-stranded or double-stranded. Probes are useful in the detection, identification and isolation of particular gene sequences or fragments. It is contemplated that any probe used in the present invention can be labeled with a reporter molecule so that it is detectable using a detection system, such as, for example, ELISA, EMIT, enzyme-based histochemical assays, fluorescence, radioactivity, luminescence, spin labeling, and the like.

The terms "array", "polynucleotide array", "microarray", and "probe array" all refer to a surface on which is attached or deposited a molecule capable of specifically binding a polynucleotide of a given sequence. Typically the molecule will be a polynucleotide having a sequence complementary to the polynucleotide to be detected, and capable of hybridizing to it.

General Method:

One of the important uses of the large Chemogenomics database to derive drug and compound signatures. Signatures are lists of genes and coefficients that relate responses of organisms or cells to the action of drugs and compounds. In order to derive signatures relating the response of an organism or cell to drugs, drug-classes, drug mechanism of action, drug-class mechanism of action, drug target pairs, drug toxicology, drug-class toxicology and drug-class target pairs one can take advantage of the contextual and structure activity relationships present in large-chemogenomic expression databases like that described above. These signature types can be derived using other alternative methods including: decision trees and its variants, Bayesian methods and variants, neural networks, support vector machines and other linear discriminate analysis methods, and analysis of variance techniques (ANOVA), and the like. Presently preferred are the methods of support vector machines. These methods are discussed in some details in T. Hastie et al., supra.

A Example Derivation of Signatures using Distinction-Ranked Methods: Alternatively, the Group Signature can be defined by performing a distinctiveness calculation to determine which genes distinguish the experimental group best from the counter group. For example, one can employ the distinction metric set forth by T. R. Golub et al., Science 286(5439), 531-37 (1999), where distinction is calculated as $$(\text{mean}_1-\text{mean}_2)/(\text{stdev}_1+\text{stdev}_2)$$

where $\text{mean}_1$ and $\text{stdev}_1$ refer to the mean expression level and standard deviation of expression levels for gene "1". This calculation will generally produce a very similar (although not necessarily identical) set of genes for the Group Signature. It is presently preferred to use a modified form of the Golub metric, where distinction is calculated as $$(\text{mean}_1-\text{mean}_2)/(\text{stdev}_1+\text{stdev}_2+c)$$

where c is a small value such as 0.1, in order to avoid errors in cases where the standard deviation (stdev) terms in the denominator are zero or close to zero. This happens often by chance when a small number of experiments are used to define the groups. The problem is exacerbated when the data is filtered by a quality control metric and the non-statistically significant ratios are reset to one (Log ratio=0). The small value of 0.1 added to the denominator can be modified for linear ratios ($\log_{10}$ of the ratio is presently preferred). We refer to signatures generated by this calculation as "t-ranked" signatures.

Preferred Alternative methods to derive signatures: Alternatively, one can employ other techniques such as support vector machines ("SVM") to determine a set of genes and weights that closely specify a characteristic expression pattern. See, for example, Barnhill, U.S. Pat. No. 6,427,141; Burges, U.S. Pat. No. 6,134,344; Mendrick et al., US Appln. Pub. No. 2002/0119462 (A1); Califano et al., US Appln. Pub.

No. 2002/0042681 (A1); Huyn, US Appln. Pub. No. 2002/0095260 (A1); and Rocke et al., US Appln. Pub. No. 2002/0111742 (A1), each incorporated herein by reference. Other alternative methods may also provide similar findings including: decision trees and its variants, Bayesian methods and variants, neural networks, and analysis of variance techniques. These methods are discussed in some details in T. Hastie et al., supra.

Drug signatures and compounds signatures represent subdivisions of the gene expression pattern. The relationship is built with reference to those part of a gene expression pattern that can be assigned coregulated and anti-coregulated genes that can be associated with specific compounds, compound-classes, compound mechanisms of action, compound-class mechanism of action, compound target pairs, compound toxicology, compound-class toxicology, and compound-class target pairs. Signatures frequently are comprised of genes related to one another by a pathway or process relationship. Signatures represent a sub-division of the biological response of a compound. Compounds with similarity to each other by a signature may be hypothesized to stimulate similar biological process or pathways. Signatures simplify data interpretation, since they group together genes and events that are related. However, many compounds have more than one signature representing different aspects of its biological effect. FIG. 1 is a hypothetical display of expression data that conceptually illustrates how signatures help data interpretation.

In many scientific situations, in particular with gene expression data from microarrays, it is desirable to be able to calculate a score function that evaluates the relationship between one or more experimental measurements taken over many dimensions and a representative, or signature, expression of a characteristic set of measures representing a specific experimental condition or property or representing an evaluation of the relative standing of the experimental relationship between two reference measurement vectors. The Signature Projection Score is a method of creating and calculating a score function for measuring the relationship between these situations.

Assume that measurements are taken on a scientific process under study under a number of experimental conditions. For instance, tissue samples could be taken from a number of experimental animals, each subjected to a dose regime of a specific drug over a specific length of time. Each measurement is assumed to be multidimensional over a large set G of measurement dimensions. For instance, each tissue sample could then be hybridized onto a microarray, and measurements taken of the mRNA abundance of many specific genes. Additional measurements may also be taken on other data domains, such as blood chemistry measurements or histopathology scores. The only requirement is that these measurements are in interval numerical form. For purposes of this discussion all such measurement dimensions are combined in G. Measurements may be subjected to appropriate data transformations and summarizations before analysis. For instance, the average logarithm of the ratio of the gene expression between several animals dosed at a specific level and corresponding control animals can be used as the basis for this analysis. We define a "signature" as a specified subset $G_S$ of the dimensions of G which are most affected, or characteristic, of an effect of interest or of the comparison between two specific effects of interest. (The former case can be thought of as a specific sub-case of the latter, wherein one of the two experimental conditions to be compared is the null condition). Additional information can be associated with a signature, indicating such things as the importance weight of each dimension, and the direction of change associated with the comparison.

A "signature score" is a method of calculating, for any given signature and any given set of measurements on an experimental condition, the size of the specific effect associated with that signature expressed under that experimental condition.

The "Signature Projection Score" is a specific method of calculating a signature score. If the (possibly transformed and summarized, as above) measurements on an experimental condition c to be evaluated are $X_g^c$, for g in G, then the signature score for that condition with respect to a signature over genes $G_S$ is calculated as $$SPS(c) = \sum_{g \in G_S} \frac{(X_g^c - R_g)(T_g - R_g)}{S_g}$$

Here ($T_g$, $R_g$, $S_g$, $g \in G_S$) are associated parameters of the signature, with the following interpretations:

The values of $T_g$ represent the treatment or effect of interest on the specific measurement dimension g. In the case of signatures for average log ratio gene expression these could be computed as the average measurement of the across the signature dimensions among the treated group of interest.

The values of $R_g$ represent the reference, or control, or null state of the signature in the specific measurement dimension g. In the case of signatures for average log ratio gene expression and for distinguishing a single effect of interest, these values will often be 0. In the case of comparing two effects, the $R_g$ can be computed as the average measurement across the signature dimensions among the reference group. Alternatively, in cases where the Signature Projection Score is to be calculated for a linear classifier such as calculated from support vector machines, $R_g$ can be chosen to correspond to the boundary of the classification rule, such that the linear classification decision would be correspond to the sign of the Signature Projection Score.

The values of $S_g$ represent scaling factors for the contribution of each measurement dimension to the signature score. In the simplest case, the value of $S_g$ is the same for each dimension, and is chosen in such a way that the SPS score for a particular condition or maximum across a particular set of conditions (e.g. the set of conditions used to derive the signature) achieves a specified outcome value, e.g. 100. Alternatively the values of $S_g$ can be adjusted in order to differentially weight the signature dimensions for the precision and accuracy of that measurement dimension. Options for this adjustment might be the between or within condition variances of the measurements on that dimension among the relevant conditions to this signature. For any signature method such as support vector machines that yields a linear discriminant classification rule the gene weights of the linear classifier can be easily translated into corresponding values of $S_g$ such that the linear classification rule can be expressed as a Signature Projection Score. In all cases a final consistent scale factor is applied to the $S_g$ in order that the specified outcome value is achieved on the specified condition.

If several conditions are to be evaluated conjointly over a set of treatment conditions C, the score for the entire set can be evaluated by summarizing the SPS score over the individual conditions in various ways, for instance the maximum can be taken over all conditions:

$$SPS(C) = \max_{c \in C} \left\{ \sum_{g \in G_s} \frac{(X_g^c - R_g)(T_g - R_g)}{S_g} \right\}$$

Alternatively the score with the largest absolute value can be chosen. Other options are also possible.

A similarity between any gene signature and the expression profile arising from treatment of a test subject with a particular compound can be calculated using a variety of methods, including distance metrics in common use, like Euclidean distance, or Pearson's correlation coefficient or other similarity measurements as discussed in for example: T. Hastie et al., supra. However for the purposes of relating the similarity of signatures we find that a Signature Projection Score (SPS) metric defined here is preferable.

Using only the genes in the signature, the amount and direction of gene expression changes in an experimental sample are compared (in terms of log ratio of expression signals) against a reference gene expression change (computed as the average over a characterizing set of treatments in our database). The sum over genes of the product of these two differences is computed, and normalized such that the highest score of any of the characterizing treatments when calculated in this way is 100.

One way to visualize this is to take the two vectors of gene expression (shown in FIG. 2), experimental and reference, and take the length of the perpendicular projection of the experimental vector onto the reference vector, divided by the length of the reference vector, as a percent. So if the experimental and reference vectors are closely aligned, you get a large signature score, if they are at right angles you get a small signature score. This is of course very much like a correlation between these two vectors, but here the normalization is only with respect to the reference vector, so that we can evaluate the magnitude of the experimental effect in the direction of interest, not just its direction (if we used correlation, a very small effect that happened to be co-aligned with the signature vector would get a correlation of 1, as would a very large effect in the same direction).

Figure 2:
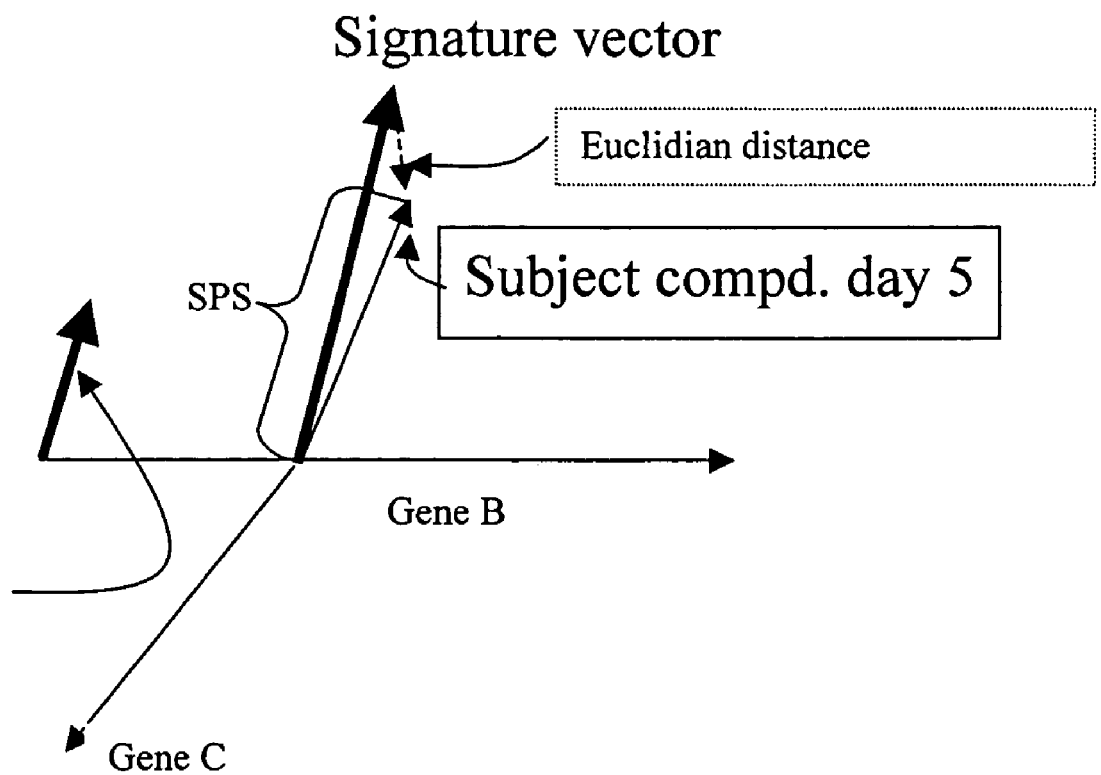
FIG. 2 depicts an illustration of the projection of a genomic expression vector against a signature vector, illustrating the derivation of the Signature-Projection Score.

FIG. 2 shows an example with a three gene signature and labels indicating the vector meaning of the SPS as compared to the signature vector, and contrast on the figure the meaning of a correlation coefficient measurement of similarity (a slope factor), or the Euclidian distance meaning of similarity are shown in FIG. 2. A three gene signature is shown for simplicity; however, the SPS equation shown above contemplates a multi-dimensional relationship with each gene of the signature comprising a dimension. Likewise, the correlation coefficient measurement method or the Euclidean distance method could be extended to the multi-dimensional case.

This method is advantageous over the correlation coefficient method because it takes into account the amplitude of the expression changes as well as their direction; it is superior to Euclidian distance methods because it measures direction and magnitude relative to the untreated or control state and not just the distance between a test compound and some standard compound treatment.

Advantages of the Signature Projection Score (SPS) over other measures include:

It provides a number that relates a compound's gene signature to other compounds and compound families.

It reflects both the intensity of the effect and the closeness of match.

Hypermatches as well as anti-matches to the signature property can be evaluated.

It has an intuitive interpretation feel.

It can be rapidly and easily calculated.

Standard error calculations easily can be performed to represent the uncertainty of the score.

The statistical significance of the finding (p value) can be easily computed.

These properties would not hold for other traditional measures of similarity, such as Pearson correlation or Euclidean distance. Pearson correlation derives only from the similarity of the direction of change (the angle between the two vectors), and does not evaluate the magnitude of the change. Hence it would be impossible to distinguish a small effect in the direction of interest from a large one. Euclidean distance evaluates only the distance between the compound and signature vectors, so a) it does not focus on in the dimensions relevant to the signature, and b) it would score increasing distance (i.e. decreasing similarity) if the compound showed more activity in the direction of the signature than the cases used to build the signature. Other measures of similarity currently in use share similar deficiencies relative to the Signature Projection Score.

The Group Signature is useful for identifying the gene regulatory pathways and processes most affected by the compounds in the experimental group, and by extension the genes most involved in the response to the compounds and/or the biological effect induced by the compounds, particularly when combined with pharmacological assay, clinical chemistry, animal blood cell measurements, and histopathology information regarding the effect of the compounds on a variety of known enzymes and binding proteins.

The Group Signature is also useful for classifying or characterizing a new compound based on its genomic expression pattern, and predicting the potential therapeutic activity thereof. Comparing the expression pattern of several thousand genes in response to a compound with the expression patterns of several thousand genes to a large number of other compounds is a very calculation-intensive activity. However, one can compile a database of Group Signatures, having one or more signatures for each class of therapeutic compound (for example, a fibrate signature, an ACE inhibitor signature, a caspase inhibitor signature, and the like), where each signature need only include, for example, 10 to 20 gene expression patterns. The resulting Group Signature database is much smaller than a complete database of genomic expression patterns, and can be queried rapidly. Genes that have not been selected to comprise any Group Signature in the database need not be examined at all; this comprises a main advantage of this approach as compared to whole gene expression pattern approaches.

The Group Signature is also useful for classifying or characterizing a new compound based on its genomic expression pattern, and predicting the potential toxicological activity thereof. Comparing the expression pattern of several thousand genes in response to a compound with the expression patterns of several thousand genes to a large number of other compounds is a very calculation-intensive activity. However, one can compile a database of Group Signatures, having one or more signatures for each class of toxic compounds (for example, a metal toxicity signature, an halogenated solvent signature, a peroxisome proliferation signature, and the like), where each signature need only include, for example, 10 to 20 gene expression patterns. The resulting Group Signature database is much smaller than a complete database of genomic expression patterns, and can be queried rapidly.

Genes that have not been selected to comprise any Group Signature in the database need not be examined at all; this comprises a main advantage of this approach as compared to whole gene expression pattern approaches.

Further, Group Signatures can be directly "embodied" in a probe set (whether in a polynucleotide array or in solution phase) and other detection reagents. For example, a substrate can be provided with a plurality of group areas, each group area containing polynucleotide sequences capable of specifically binding sequences present in a specific Group Signature. Thus, a Group Signature Chip may have a first region containing probes specific for the fibrate Group Signature, a second region containing probes specific for the phenyl-acetic acid (for example, aspirin, naproxen, ibuprofen) Group Signature, and so forth. The probes for each Group Signature are preferably selected so that they do not overlap, or overlap to a minimal degree. Alternatively, if two or more Group Signatures include a common set of genes, the chip can be arranged to include probes for the common set as the intersection between two signatures, for example so that Signature 1 comprises region 1 plus common region X, and Signature 2 comprises region 2 plus common region X. These overlapping Group signatures may have relationships other than a common direction of change; for example, the common region X may need to be induced (expression increased) in Signature 1 but repressed (expression decreased) or remain unchanged in Signature 2. The Group Signatures present on the chip can include both signatures from therapeutic drugs, and signatures of specific modes of toxicity. Thus, mRNA or cDNA can be obtained from a test subject after exposure to a test compound, labeled, and applied directly to the Group Signature Chip: the activity(ies) and toxicity of the test compound (if any) is then identified directly by determining which Group Signatures exhibit binding. It is presently preferred to provide a separate chip for each different animal species studied (for example, one chip can carry polynucleotide sequences capable of hybridizing to rat cDNA or mRNA, while another chip is provided to hybridize to mouse or human cDNA or mRNA).

Individual compounds can be examined to provide specific Drug Signatures capable of distinguishing between members of the same group (to the extent that the test subjects are capable of exhibiting a distinct response between the members). By selecting genes that distinguish a selected compound from other compounds in its group from the sorted list of genes from which the Group Signature is derived, one can obtain a Drug Signature that indicates how the subject cell responds differently to the selected compound. The Drug Signature is useful for identifying toxicities and side effects that are peculiar to the selected compound, as well as possible synergistic effects between compounds. In situations where human samples have been prepared from patients treated with various related drugs. Drug Signature can be used to explain or determine why one compound has greater or lesser activity, and/or why one compound would be a better therapeutic choice for a particular patient (based on the patient's condition).

The invention is based on the use of chemogenomic expression data, collected in response to an experimental condition, preferably from contact with a compound or bioactive substance. Suitable compounds include known pharmaceutical agents, known and suspected toxins and pollutants, proteins, dyes and flavors, nutrients, herbal preparations, environmental samples, and the like. Other useful experimental conditions to examine include infectious agents such as viruses, bacteria, fungi, parasites, and the like, environmental stresses such as starvation, hypoxia, temperature, and the like. Other useful experimental conditions to examine include situations where in the level of a particular gene product is altered, such as by providing extra copies of the gene via transfection or transgenic technology, or by providing a specific transcript reduction agent such as RNAi, a ribozyme or anti-sense RNA constructs. It is presently preferred to analyze a variety of compounds and/or experimental conditions simultaneously, particularly where many of the compounds and/or conditions are related by activity or therapeutic effect. The experimental conditions are applied to a test subject having a genome, preferably a mammalian cell, tissue or animal. Eukaryotic test subjects can be tested either in vivo or in vitro. Suitable eukaryotic subjects include, without limitation, human, monkey, rat, mouse, cow, sheep, dog, cat, chicken, pig, goat, and the like. It is presently preferred to examine mammalian test subjects using a plurality of different tissue types, for example, liver, kidney, bone marrow, spleen, and the like. The test subjects are preferably exposed to a plurality of experimental conditions, for example, to a plurality of different concentrations of a compound, and examined at a plurality of time points.

The chemogenomic response can be obtained by any available means, for example by employing a panel of reporter cells, each group of cells having a reporter gene operatively connected to a different selected regulatory region. Alternatively, one can employ primary tissue isolates, cells or cell lines lacking reporter genes, and can determine the expression of a plurality of genes directly. Direct detection methods include direct hybridization of mRNA with oligonucleotides or longer DNA fragments such as cDNA or even fragments of cloned genomic DNA (whether in solution or bound to a solid phase), reverse transcription followed by detection of the resulting cDNA, Northern blot analysis, and the like. One can employ target amplification methods (for example, PCR amplification of cDNA using Taqman® polymerase, and other enzymatic methods) and/or signal amplification methods (for example, employing highly-labeled probes, chromogenic enzymes, and the like). Polynucleotide probe arrays for expression monitoring can be made and used according to any techniques known in the art. See for example, D. J. Lockhart, et al., Nature Biotechnol (1996) 14:1675-80; G. McCall, et al., Proc Natl Acad Sci USA (1996) 93:13555-60; and U.S. Pat. No. 6,040,138, all incorporated herein by reference. It is presently preferred to measure the genomic response by means of a nucleotide array, such as, for example, GeneChip® probe arrays (Affymetrix Inc., Santa Clara, Calif.), CodeLink™ Bioarray (Motorola Life Sciences, now a product of Amersham Biosciences), and the like. Polynucleotide probes for interrogating the tissue or cell sample are preferably of sufficient length to specifically hybridize only to appropriate, complementary genes or transcripts. Typically, the polynucleotide probes will be at least 10, 12, 14, 16, 18, 20 or 25 nucleotides in length. In some cases, longer probes of at least 30, 40, 50 or 60 nucleotides will be desirable. The genes examined using the array can comprise all of the genes present in the organism, or a subset of sufficient size to distinguish the genomic expression modulation due to compounds to the degree of resolution and/or confidence desired. The method of the invention is also useful for determining the size of a sufficient subset of genes necessary for this purpose.

The data obtained, whether resulting from the array experiments or otherwise, is generally expressed in terms of the amount or degree of gene expression, and whether it is significantly upregulated or down-regulated. The data may be subjected to one or more manipulations, for example to normalize data from an array (comparing data from points in different regions of the physical array, to adjust for systematic errors; normalization can also adjust for probe labeling differences between individual arrays and other similar type array to array variations). Data is frequently presented in the form of a ratio, for example the experimental expression level compared to the control level, where the control level can be the untreated expression level for the same gene, a historical untreated level, a pooled expression level for a number of genes, and the like. Each data point is associated with a compound (or control), a gene or polynucleotide sequence corresponding to the mRNA detected, and an expression level, and can further comprise other experimental conditions such as, for example, time, dose, temperature, subject animal species, subject animal gender, subject animal age, other treatment of the subject animal (such as fasting, stress, prior or concurrent administration of other compounds, time and manner of sacrifice, and the like), tissue or cell line from which the data is derived, type of array and serial number, date of experiment, researcher or client for whom the experiment was performed, and the like.

Experimental Procedures of the General Method:

Compound dosing was based on the acute dose $LD_{50}$s recorded in published reference or literature sources. Duplicate rats were dosed at each of 3 doses: at $LD_{50}$, one-half and one-fourth of $LD_{50}$. The MTD (maximum tolerated dose) was then selected as the dose at which the animals put on 5-10% body weight during the 5-day range finding study. Vehicle dosed animals put on 18-25% body weight during this time. In addition, the clinical observations must show no or mild clinical signs during the whole of the range-finding study. At the next highest dose, signs and symptoms of adverse effects and exceeding those of the MTD should be seen to occur. Should these criteria not be met, the range-finding study is repeated using a modified dose range. During the full study, reconfirmation of the range finding studies MTD conclusions was confirmed using the same observations. In addition, clinical chemistry and histopathology data was collected in order to assess the level of toxic events that this dose actually displayed. Another dose was also selected for study, the fully effective dose (FED), selected as that dose which, from literature reports, fully cures or corrects an animal model of the disease for which the drug is used in humans.

After determination of the MTD and FED for a compound, each compound was dissolved in a vehicle for administration on day 1 of the study (additional daily doses were stored as frozen aliquots from this initial formulation). Each compound was administered to three individual male Sprague-Dawley rats for each of the two doses (MTD and FED) for one of four different times (0.25 day, 1 day, 3 days, and 5 days), yielding a total of up to 24 animals per compound study. Vehicle choice was based on solubility of the compound, effect of food on adsorption, and the vehicles used in the literature reports examined during the FED selection investigations, described above. Generally, the route and vehicle in which the FED was defined are used. When there was a choice of routes and vehicles, oral routes were chosen over injection routes. Many compounds, especially oncolytics, are only administrable intravenously. In such cases, the compound was administered as an intravenous formulation into the tail vein. Orally administered compounds were given dissolved in either water, 1% carboxymethycellulose (CMC) or corn oil. Intravenously and intraperitoneally administered compounds were given in 0.9% saline. Subcutaneously administered compounds were given in corn oil. Animal body weights were determined at 1 day and, where appropriate, at 4 days, before necropsy, and clinical observations were made on a daily basis. Control animals were dosed with vehicle only. Three male animals were used for each dose and time combination used for the compound treatment.

Tissue harvest and handling: After the allocated treatment time, the tissues from the animals were harvested. The animals from 0.25 day and 1 day treatment had 5 tissues collected (liver, kidney, heart, bone marrow, and one additional tissue which was selected on the basis of literature reports on the compound's toxicology, or brain was collected in the absence of any literature data). The animals from 3 day and 5 day treatments had 12 tissues collected (liver, kidney, heart, bone marrow, spleen, brain, stomach-fore, stomach-glandular, intestine, muscle, lung, gonads), and in addition blood was collected for and was analyzed for both clinical chemistry and hematology components. All the tissues collected were divided to provide samples for histopathological analyses, and the remainder of each tissue was then snap-frozen.

Clinical chemistry: Parameters were measured on blood samples from all animals that had been exposed to compound for 3 days or 5 days. The parameters were measured using a Hitachi-911 clinical chemistry analysis instrument according to the manufacturer's instructions. The following blood constituents were measured: Blood Urea Nitrogen (BUN), Creatinine (CRE), Glucose (GLU), Alanine Transaminase (ALT), Aspartate Aminotransferase (AST), Alkaline Phosphatase (ALP), Total Bilirubin (TBI), Sodium (SOD), Potassium (POT), Chloride (CHL), Phosphorus (PHO), Total Protein (TPR), Albumin (ALB), Cholesterol (CHO), Creatine Phosphokinase (CPK), Lactate Dehydrogenase (LDH), Carbon Dioxide (CO2), Uric Acid (UA), and Lipase.

Hematology: Parameters were measured on blood samples from all animals that had been exposed to compound for 3 days or 5 days. The parameters were measured using a Baker 9000 blood cell analysis instrument according to the manufactures instructions. The following blood constituents were measured: Leukocyte count (WBC), Differential Leukocyte counts, Erythrocyte count (RBC), Hemoglobin concentration (HGB), Hematocrit (HCT), Mean Corpuscular Volume (MCV), Mean Corpuscular Hemoglobin (MCH), Mean Corpuscular Hemoglobin Concentration (MCC), Thrombocyte Count (PLC).

Histopathology: Histopathological analyses of hematoxylin and eosin-stained tissue sections were performed and peer-reviewed by board-certified (Diplomate, American College of Veterinary Pathologists) veterinary pathologists.

Preparation of enriched mRNA: Punch biopsies were taken from the frozen tissues and were completely homogenized before being processed using the MagNA Pure robot. (Roche Diagnostics Corp., Indianapolis, Ind.) in combination with the MagNA Pure LC RNA Isolation kit II (Roche Diagnostics Corp). The amount of lysis buffer was adjusted to allow 1 ml per 50 mg for liver tissue, or 1 ml per 80 mg for all other tissues. After complete homogenization and before loading of the samples into the 32-well MagNA Pure plate, the samples were syringed 5-6 times using a 20-gauge 3-ml syringe to ensure a smooth solution for robotic processing. Tissue sample processing was performed in duplicate wells (loading 150 µl of homogenized sample and 150 µl of additional lysis buffere to each well) of the MagNA Pure LC, which is programmed to extract mRNA using oligo-dT selection technology into a final elution volume of 100 µl. Poly A(+) RNA sample concentration was performed using a standard ethanol precipitation protocol in the presence of glycogen (50 µg/ml). After precipitation the final purified mRNA sample was resuspended in 7 µl DEPC-treated water and quantified using a Ribogreen high-range assay (Molecular Probes) on the Victor-Wallace II Fluorometer (Perkin-Elmer). Additionally, the integrity of each mRNA sample was determined using the Agilent 2100 BioAnalyzer (Agilent Technologies, Palo Alto, Calif.) in combination with the RNA 6000 Nano Lab Chip kit (Agilent Technologies).

Hybridization Probe Preparation: The methods used for cRNA preparation are essentially as described in the CodeLink manual v2.1 as supplied by Motorola Life Sciences (D. R. Dorris, et al., *Genome Res* (2002) 12:976-84) using the Qiagen BioRobot 9604, with the exception that enriched mRNA was used as the starting material instead of total RNA. 0.6-20 µg of enriched mRNA from different tissue sources was processed into cRNA in the presence of different bacterial control mRNAs (1.5 pg FixA, 5 pgYjek, 5 pg AraB, 15 pg EntF, 50 pg FixB, 150 pg HisB, 500 pg LeuB, 1500 pg Gnd) and with the modification of the addition of 1.0 µl of 100 µmol/µl HPLC-purified T7-$(dT)_{24}$ oligonucleotide primer instead of a 0.5 pmol/µl unpurified T7-$(dT)_{24}$ primer.

Hybridization to Micorrays: 10 µg of fragmented cRNA was used for hybridization onto CodeLink™ microarrays (Motorola Life Sciences, now a product of Amersham Biosciences) using the protocol described in R. Ramakrishnan et al., *Nuc. Acids Res* (2002) 30:e30. After an 18 hour hybridization at 37° C., the 12-slide shaker tray was removed from the Innova™ 4080 shaker, and the hybridization chamber taken off each slide. Each slide was placed into the BioArray Rack of the Parallel Processing Tool (Motorola Life Sciences, now a product of Amersham Biosciences) and incubated with 0.75×TNT (0.075 M Tris-HCl, pH 7.6, 0.1125 M NaCl, 0.0375% Tween-20®) at 46° C. for 1 hour. The BioArray rack was moved from the reservoir containing TNT and transferred to a small reagent reservoir containing 1:500 dilution of streptavidin-Alexa 647 (Molecular Probes). The signal was developed for 30 minutes at room temperature, before the reaction was stopped and slides were washed four times for 5 minutes each in TNT buffer (0.1 M Tris-HCl, pH 7.6, 0.15 M NaCl, 0.05% Tween-20®) using a large reagent reservoir. The slides were rinsed in distilled, deionized water (dd-$H_2O$) with 0.05% Tween-20® twice for 5 seconds each before they were dried by centrifugation and stored in light protective slide boxes.

Microarray Data Collection: Processed slides were scanned using the Axon GenePix Scanner (Axon Instruments, Union City, Calif.) with the laser set to 635 nm, the photomultiplier tube (PMT) voltage to 600 and the scan resolution to 10 microns. Slides were scanned using CodeLink™ Expression Scanning Software (Motorola Life Sciences, now a product of Amersham Biosciences). Each slide image was analyzed using the CodeLink Expression Analysis Software (Motorola Life Sciences, now a product of Amersham Biosciences).

Microarray Data Pre-processing: Data collected from the scanner was then pre-processed in one of two ways—the Iconix Normalization approach, and the Novation Dewarping/Detrending™ normalization technique. The Novation Dewarping/Detrending™ technique uses a non-linear centralization normalization procedure (A. Zien et al., Bioinformatics (2001) 17:323 S-31S) adapted specifically for the CodeLink microarray platform (Motorola Life Sciences, now a product of Amersham Biosciences). The procedure utilized de-trending and de-warping algorithms to adjust for non-biological trends and non-linear patterns in signal response, leading to significant improvements in array data quality. Novation Dewarping/Detrending™ recruits all low abundance signals consistent with the two-channel patterns to avoid threshold distortions and adds dewarping leverage. Hence, threshold failed elements are retained if they tend to support the patterns. De-trending is performed by first applying statistical response surface methodologies (R. Myers and D. Montgomery, "Response surface methodology: process and product optimization using designed experiments" (1990, Wiley Series in Probability and Statistics, NY)) to correct bias category. Next a non-linear centralization normalization algorithm (or de-warping) is applied to correct bias category. The procedure assumes that either of two conditions is fulfilled: (i) most genes are not or only moderately regulated (ii) approximately equal numbers of genes are up regulated as are down regulated. Nonlinear signal patterns are corrected by comparing signal intensities from each test array to the signal intensities of the "non-regulated" genes obtained from a collection of pooled reference arrays. This reference set was obtained by pooling signal intensities from "non-regulated" genes across hundreds of arrays generated under controlled experimental conditions. For each test array, Dewarping/Detrending™ generated the two-sample concordance plot of log probe signal intensities for the experimental array versus the log probe signal intensities for the "non-regulated genes" on the reference array. Dewarping/Detrending™ then formed a 2-dimensional histogram by binning both axes and plotting the frequency of occurrence on a third axis. The resulting 3-dimensional histogram represents the density of points in the original scatter plot, with the frequency density resembling a mountain range. The major mode of this histogram is an elongated ridge formed by the population of "non-regulated" genes ranging over their typical variations in abundance, which provides a useful definition of expression baseline. The normalization procedure then mathematically transforms this ridge into a straight line and rotates it to the diagonal position. The final corrected (or "de-warped") concordance plot has the expected pattern for the population of "non-regulated" genes from two reporter channels.

Details of the experimental conditions and process parameters are entered into a centralized laboratory information management system (LIMS). The identifiers in the data file drive a validation process that assures we have complete LIMS information for each sample. The microarray signals in the data file are then loaded into a Oracle database tables designed to hold raw signal data from several types of microarray platforms. Loading of these data triggers the data processing pipeline that normalizes the data using scaling and dewarping algorithms, loads spot quality counts, computes other metrics for quality assessment, associates these data with other biological replicates and matched controls and computes log ratios of gene expression changes and related statistics.

$Log_{10}$ ratios are computed as the difference of the logs of the averaged experimental signals less the averaged control signals for each gene. To assign a significance level to each gene expression change, the standard error for the measured change in the experiments and controls is computed. To do this requires an estimate for sigma, which is difficult with a small number of replicates (in this case, 3). To get a better estimate of sigma, and therefore a better estimate of standard error, an empirical Bayesian estimate of standard deviation is used, which is essentially a weighted average of the measured standard error for the experiments and a global estimate of standard error for each gene determined over thousands of arrays (B. P. Carlin, and T. A. Louis, "Bayes and Empirical Bayes Methods for Data Analysis" 2nd Ed. (2000, Chapman & Hall/CRC, Boca Raton); A. Gelman et al., "Bayesian Data Analysis" (1995, Chapman & Hall/CRC, Boca Raton)). This Bayes estimate gives a more precise estimate of standard error. The standard error is used in a T-test to compute a P-value for the significance of each gene expression change. In addition, a related value, "differentness", which uses a T-test to determine if the inferred distribution of actual measurements is different from the distribution of measurements for all other genes in that experiment.

Various computer systems, typically comprising one or more microprocessors, can be used to store, retrieve, and analyze information obtained according to the methods of the invention. The computer systems can be as simple as a stand-alone computer having a form of data storage (i.e., a computer-readable medium, such as, for example, a floppy disk, a hard drive, removable disk storage such as a ZIP® drive, optical medium such as CD-ROM and DVD, magnetic tape, solid-state memory, magnetic bubble memory, and the like). Alternatively, the computer system can include a network comprising two or more computers linked together, for example through a network server. The network can comprise an intranet, an Internet connection, or both. In one embodiment of the invention, a stand-alone computer system is provided with a computer-readable medium containing a Group Signature database thereon, said Group Signature database comprising one or more Group Signature records. The computer system preferably further comprises a processor and software that enables the system to compare gene expression and/or pharmacological data from an experiment with the contents of the Group Signature database. In another embodiment of the invention, a computer is provided with a computer-readable medium containing a Group Signature database thereon (a database server), and a network connection over which other computers can connect (user systems). Preferably, the user systems are provided with processors and software for receiving and storing gene expression and/or bioassay data from one or more experiments, and for formulating database queries for transmission over the network and execution on either the database server or on the user system. The computer system can further be linked to additional databases such as GenBank™ (NCBI, Besthesda, Md.) and DrugMatrix™ (Iconix Pharmaceuticals, Inc., Mountain View, Calif.).

Data Analysis to uncover Drug Signatures™: When visually examining datasets derived from several hundred or more genes, it is presently preferred to select the genes that exhibit the greatest variability in expression level during a large number of test treatments encompassing 10 to more than 100 compound treatments. We have found that for most compounds only a few genes respond to a high degree (for example, an increase in expression level by a factor of five or more; or more preferably, change in expression by a statistically significant amount as judged by an appropriately corrected t-test), and approximately 100 to 500 exhibit a lesser but still substantial response. Most genes do not significantly respond, and can be excluded from the remainder of the analysis without loss of information. The observed variability in expression level can be adjusted for the available "dynamic range" of each gene: for example, if gene A exhibits a maximum change in expression level of only a factor of 2, and gene B exhibits a maximum change in expression level of a factor of 30, one expects that gene A at 2 (100% of maximum range) is exhibiting a stronger relative response than gene B at 4 (13% of maximum range). Accordingly, the genes can be selected based on the ratio of their observed variability (for example, standard deviation) to their possible variability (for example, the greatest degree of variation observed historically, for all experiments). It is presently preferred to order the genes by variability, and to select the 500 most variable genes for the remainder of the analysis.

It is typical for genomic expression experiments to present data in the form of a two-dimensional table or matrix, where each gene is allotted a row, and each column corresponds to an experiment or experimental condition. In contrast, the method of the invention allots a row to each compound as the row variable, and a column to each gene. The data records are then clustered by compound, thus grouping all compounds (and optionally by experimental conditions) on the basis of similar gene expression modulation. This permits one to directly identify which genes are most affected by the presence of the compounds used.

It is presently preferred to select a variety of related compounds (the "experimental group"), together with several compounds unrelated to the experimental group ("counter group") for examination and analysis under a variety of experimental conditions, such as, for example, a plurality of time points post-administration. The compounds included in the experimental group are preferably related by virtue of having similar mechanisms of action (or are believed to act by the same pathway). For purposes of developing a group signature, it is presently preferred to select at least two compounds for the experimental group, at a plurality of different experimental conditions (for example, each compound examined at several time points). The maximum number of compounds that can be included in the experimental group is typically limited by the number of related compounds available, but in any case is preferably limited to no more than 200. The number of compounds included in the counter group is preferably at least two, more preferably at least 10, and preferably no more than 200, preferably less than 100, most preferably less than 50. Preferably, the counter group is selected so that it does not contain a group of related compounds larger than the number of related compounds in the experimental group.

Pre-analysis Visualization of the Group Relationships and Derivation of Simple Eigenvalue-based Signatures: The compounds are tested and the resulting data is treated as described above, and then preferably analyzed by principal component analysis (PCA), hierarchical clustering, or one or more of a number of related clustering techniques to determine the sets of treatments (experiments) that form resolvable clusters. Once it is established which treatments can form resolvable clusters one can determine the genes or groups of genes which are most responsible for the observed effect of the compound. Several methods for achieving this goal are presented below. If the compounds selected for the experimental group are related by activity, their data points will form a distinct cluster in PCA analysis, separate from the data points belonging to the counter group (which may or may not form one or more clusters, depending on the compounds selected). The experimental group will typically dominate one PCA axis, with most, or all, of the counter group situated at lower values along the axis. The eigenvalues for the genes comprising the corresponding PCA axis can then be examined to determine which genes are modulated to the greatest degree by the experimental group: this group of genes provides a pool from which the Group Signature is determined. The Group Signature comprises a set of genes capable of distinguishing the group activity (the common biological activity exhibited by the compounds in the experimental group) from other activities. If the genes included in the PCA axis that corresponds to the experimental group activity are sorted and ranked by eigenvalue (in other words, in order of their contribution to that principal component), the genes that sort to the top of the list will comprise the Group Signature. The Group Signature need not include all of the genes ranked at the top, but should include at least the top three, and preferably further includes at least five of the top ten, more preferably at least 10 of the top 20 genes.

Post-derivation Checks and Further Refinements: If desired, the Group Signature can be further refined by comparing the expression patterns of two or more compounds at opposite ends of the PCA axis along which they spread, for example selecting a compound having a high degree of a known bioactivity and a second compound having a low degree of the same bioactivity. If the genes (already sorted for selection as part of the Group Signature) are then compared for variation between these two selected compounds, one can identify the genes that correlate most closely with the bioactivity of the compounds in the group.

It is sometimes helpful to examine the original data using PCA, to determine if any systematic errors are present. For example, if the data clusters according to experiment date, lab technician, or the like, further analysis of the data is typically warranted. It is useful to note that a systematic bias can occur that separates all treatments into subgroups (along a PCA axis for example), yet this does not preclude the detection and visualization of underlying biological effects. This capacity of PCA to group experiments in three dimensions, and thus to visualize multiple simultaneous effects including systematic biases, is a marked advantage compared to other methods such 2D hierarchical clustering, where a single dimension is used to cluster experiments and the other dimension is used to cluster the genes.

Analysis of Specificity of each Gene to a Particular Signature: A specificity can be calculated for each signature by comparing the expression level of each gene in the signature with the probability of occurrence across all of the experiments, and adding or multiplying the probabilities to obtain a score (where, like a p value, the smaller number indicates a greater specificity). For example, in a signature consisting of upregulated genes A, B, and C, if the induction level for gene A in an experiment is reached (or surpassed) 1% of the time, the expression level for gene B is reached (or surpassed) 3% of the time, and the expression level for gene C is reached (or surpassed) 12% of the time, the specificity would be calculated $0.01 \times 0.03 \times 0.12 = 0.000036$. If genes A, B, and C exhibited their expression levels more often, for example 4%, 6%, and 15% respectively, the resulting score would be lower ($0.04 \times 0.05 \times 0.15 = 0.0003$), because the gene expression levels would be less distinctive or characteristic. The signature specificity can be further refined by weighting the score: the genes that are ranked lower in the signature are less important, and less distinctive than those ranked higher. Thus, for example, one can calculate a weighted specificity by dividing the probability score for each gene by its rank in the signature, or by a multiple or higher power of the rank. For example, given a signature consisting of upregulated genes X, Y, and Z, wherein the induction level for gene X is reached in 1% of the experiments, the induction level for gene Y is reached in 3% of the experiments, and the induction level for gene Z is reached in 12% of the experiments, a simple additive specificity would be $0.010 + 0.030 + 0.120 = 0.160$. In a weighted specificity in which each term was divided by the gene rank, the specificity would be calculated $(0.010/1) + (0.030/2) + (0.120/3) = 0.065$. A signature in which the first gene was less predictive (higher probability) would have a higher score (indicating less specificity): for example, if the probabilities for genes X, Y and Z were reversed, the same specificity would be calculated $(0.120/1) + (0.030/2) + (0.010/3) = 0.138$.

The specificity score can be weighted more heavily by increasing its dependence on gene rank, for example using the square or cube of the gene rank as the divisor. Thus, for example, the XYZ signature can be calculated as $(0.010/1) + (0.030/4) + (0.120/9) = 0.0308$ using the square of the rank, or $(0.010/1) + (0.030/8) + (0.120/27) = 0.0182$ using the cube of the rank. Again, comparing the results with the specificity scores obtained with the probabilities reversed (0.1286 and 0.1241, respectively), one can see that the difference in score increases with increased weighting: the difference in specificity score between XYZ and "reversed" XYZ is 0.0723 for weighting by rank, 0.0978 for weighting by the square of the rank, and 0.1059 for weighting by the cube of the rank. Alternatively, one can use other weighting factors, such as for example, the gene rank raised to a non-integral power (for example, 2.1, 2.5, 4.2, and the like), the logarithm of the rank, a set of arbitrarily-selected constants (for example, using as divisor 1, 2, 4, 8, and 10 for the first five genes, and 15 for each additional gene), and the like. One can use a power <1, such as square root ($=\frac{1}{2}$): this has the effect of decreasing the weight of the rank. This in effect allows weighting over a longer signature.

Measurement of the Similarity between Signatures: A similarity between any gene signature and the expression profile arising from treatment of a test subject with a particular compound can be calculated using a variety of methods, including distance metrics in common use, like Euclidean distance, or Pearson's correlation coefficient or other similarity measurements as discussed in for example: T. Hastie et al., supra. However for the purposes of relating the similarity of signatures we find that a Signature Projection Score (SPS) metric derived as follows is a superior method $$\text{score} = \max_{t} \left\{ \sum_{g \in 1}^{\# \text{ gene}} \frac{(X_g^t - R_g)(T_g - R_g)}{S_g} \right\},$$

where $X_g^t$ are the gene expression values on the experimental compound under dose/time treatment t for gene g, $T_g$ and $R_g$ are the treated and reference gene expression levels, and $S_g$ are proportional to the expression variability for each gene and normalized such that the maximum score of any treatment among the set of treatments used to derive the score has a score value of 100.

Using only the genes in the signature, the amount and direction of gene expression changes in an experimental sample are compared (in terms of log ratio of expression signals) against a reference gene expression change (computed as the average over a characterizing set of treatments in our database). The sum over genes of the product of these two differences is computed, and normalized such that the highest score of any of the characterizing treatments when calculated in this way is 100.

One way to visualize this is to take the two vectors of gene expression (shown in FIG. 1), experimental and reference, and take the length of the perpendicular projection of the experimental vector onto the reference vector, divided by the length of the reference vector, expressed as a percentage. So if the experimental and reference vectors are closely aligned, a large signature score results, while vectors at right angles produce a small signature score. This is of course very much like a correlation between these two vectors, but here the normalization is only with respect to the reference vector, so that we can evaluate the magnitude of the experimental effect in the direction of interest, not just its direction (if we used correlation, a very small effect that happened to be co-aligned with the signature vector would get a correlation of 1, as would a very large effect in the same direction).

This method is advantageous over the correlation coefficient method because it takes into account the amplitude of the expression changes as well as their direction; it is superior to Euclidian distance methods because it measures direction and magnitude relative to the untreated or control state and not just the distance between a test compound and some standard compound treatment.

The Group Signature is useful for identifying the gene regulatory pathways and processes most affected by the compounds in the experimental group, and by extension the genes most involved in the response to the compounds and/or the biological effect induced by the compounds, particularly when combined with pharmacological assay, clinical chemistry, animal blood cell measurements, and histopathology information regarding the effect of the compounds on a variety of known enzymes and binding proteins.

The Group Signature is also useful for classifying or characterizing a new compound based on its genomic expression pattern, and predicting the potential therapeutic activity thereof. Comparing the expression pattern of several thousand genes in response to a compound with the expression patterns of several thousand genes to a large number of other compounds is a very calculation-intensive activity. However, one can compile a database of Group Signatures, having one or more signatures for each class of therapeutic compound (for example, a fibrate signature, an ACE inhibitor signature, a caspase inhibitor signature, and the like), where each signature need only include, for example, 10 to 20 gene expression patterns. The resulting Group Signature database is much smaller than a complete database of genomic expression patterns, and can be queried rapidly. Genes that have not been selected to comprise any Group Signature in the database need not be examined at all; this comprises a main advantage of this approach as compared to whole gene expression pattern approaches.

The Group Signature is also useful for classifying or characterizing the potential toxicological activity of a new compound based on its genomic expression pattern, as Group Signatures can be derived for each class of toxic compounds (for example, a metal toxicity signature, a halogenated solvent signature, a peroxisome proliferation signature, and the like), where each signature need only include, for example, 10 to 20 gene expression patterns.

An additional advantage of Group Signatures is that inasmuch as the complete gene expression profile for a new compound can be thought to be comprised of various signatures representing both efficacious and toxic events, the Group Signatures allow these various effects to be separately observed and quantitated. The less-desirable alternative is to match a new drug treatment's entire gene expression profile with that of other compounds, and likely miss the possibly subtle underlying expression patterns.

Further, Group Signatures can be directly "embodied" in a probe set (whether in a polynucleotide array or in solution phase) and other detection reagents. For example, a substrate can be provided with a plurality of group areas, each group area containing polynucleotide sequences capable of specifically binding sequences present in a specific Group Signature. Thus, a Group Signature Chip may have a first region containing probes specific for the fibrate Group Signature, a second region containing probes specific for the phenyl-acetic acid (for example, aspirin, naproxen, ibuprofen) Group Signature, and so forth. The probes for each Group Signature are preferably selected so that they do not overlap, or overlap to a minimal degree. Alternatively, if two or more Group Signatures include a common set of genes, the chip can be arranged to include probes for the common set as the intersection between two signatures, for example so that Signature 1 comprises region 1 plus common region X, and Signature 2 comprises region 2 plus common region X. These overlapping Group signatures may have relationships other than a common direction of change; for example, the common region X may need to be induced (expression increased) in Signature 1 but repressed (expression decreased) or remain unchanged in Signature 2. The Group Signatures present on the chip can include both signatures from therapeutic drugs, and signatures of specific modes of toxicity. Thus, mRNA or cDNA can be obtained from a test subject after exposure to a test compound, labeled, and applied directly to the Group Signature Chip: the activity(ies) and toxicity of the test compound (if any) is then identified directly by determining which Group Signatures exhibit binding. It is presently preferred to provide a separate chip for each different animal species studied (for example, one chip can carry polynucleotide sequences capable of hybridizing to rat cDNA or mRNA, while another chip is provided to hybridize to mouse or human cDNA or mRNA).

Individual compounds can be examined to provide specific Drug Signatures capable of distinguishing between members of the same group (to the extent that the test subjects are capable of exhibiting a distinct response between the members). By selecting genes that distinguish a selected compound from other compounds in its group from the sorted list of genes from which the Group Signature is derived, one can obtain a Drug Signature that indicates how the subject cell responds differently to the selected compound. The Drug Signature is useful for identifying toxicities and side effects that are peculiar to the selected compound, as well as possible synergistic effects between compounds. In situations where human samples have been prepared from patients treated with various related drugs. Drug Signature can be used to explain or determine why one compound has greater or lesser activity, and/or why one compound would be a better therapeutic choice for a particular patient (based on the patient's condition).

EXAMPLES

The following examples are provided as a guide for the practitioner of ordinary skill in the art. Nothing in the examples is intended to limit the claimed invention. Unless otherwise specified, all reagents are used in accordance with the manufacturer's recommendations.

Example

Leukocyte Depletion Signature (A) This signature identifies treatments by drugs that cause leukocyte depletion in an organism.

The Leukocyte Depletion Signature was derived by analysis of a subset of data from about 2000 in vivo rat drug treatments (using about 300 individual drugs) representing multiple tissues; the method for creation of this dataset is described in the general methods section. The subset used for this analysis comprised the expression data from the livers of rats treated with compounds that significantly lowered serum albumin levels by at least 25% compared with vehicle-treated control animals. These compounds (and dosages) were Methotrexate (27 mg/kg, oral gavage in saline, Doxorubicin (3 mg/kg, intravenous in saline), Chlorambucil (4.5 mg/kg, oral gavage in saline), Thioguanine (12 mg/kg, oral gavage in corn oil), Carmustine (16 mg/kg, oral gavage in water), Mitomycin C (1.7 mg/kg, oral gavage in corn oil). All of the compounds described caused leukocytes to be depleted from the circulation of the rats by at least 3 fold as compared to control rats.

Hematology Findings used as part of training treatment identification: The hematology data showed significant decreases in the leukocyte reading for compound treatments for which this signature was derived.

TABLE 1

Selected clinical chemistry and hematology data from the study animals (all data are averages of 3 animals, SD not shown)

| Compound Name | Time Point (days) | Fold Decrease in leukocytes |
|---|---|---|
| METHOTREXATE | 3 | 4.35* |
| DOXORUBICIN | 3 | 3.30* |
| DOXORUBICIN | 5 | 4.70* |
| CHLORAMBUCIL | 5 | 7.08* |
| THIOGUANINE | 3 | 3.63* |
| CARMUSTINE | 5 | 4.49* |
| MITOMYCIN C | 5 | 3.53* |

(*= p < 0.01)

Calculation of Signature: Based on the data shown in Table 1, spleen gene expression arrays were identified that were generated from tissues from the same animals which showed this reduction in leukocyte levels. The t-ranked algorithm (described above) was used to derive a gene signature, based on the gene expression changes in these training treatment conditions when compared by ratio to control (vehicle-treated) animals.

The list of probes in the calculated signature is shown in Table 2. GenBank Accession numbers are used to identify the probe sequences used to generate the probes on the array. The Best Annotation was generated by BLAST and BLAT searching of a number of public gene sequence databases, and then collating the annotations from each to identify a best annotation. Where no definitive data was returned, the annotation provided with the Codelink microarrays (Motorola Life Sciences, now a product of Amersham Biosciences) was used. Distinction values were calculated by the method described above. $T_g$ is the treated gene expression level, $R_g$=reference gene expression level, and $S_g$ is proportional to the expression variability for each gene and normalized such that the maximum score of any treatment among the set of treatments used to derive the score has a score value of 100.

TABLE 2

Leukocyte Depletion Signature Probes

| GenBank Accession Number | Best Annotation | Distinction | Mean $T_g$ | $S_g$ |
|---|---|---|---|---|
| AA800341 | Rn\|5' end/clone=RLIAA09/clone_end=5'/gb=AA800341/gi=4131496/ug=Rn.13539/len=633 | 0.904 | 0.3284 | 5.690 |
| AA800476 | Mm\|RIKEN cDNA 4930455C21 gene (4930455C21Rik) | 1.092 | 0.3727 | 5.349 |
| AA925353 | Mm\|lysosomal-associated protein transmembrane 5, clone MGC:13988 IMAGE:4037686 | 1.112 | 0.5034 | 7.094 |
| AA945898 | Mm\|RIKEN cDNA 1810038N08 gene (1810038N08 Rik) | 0.845 | 0.2440 | 4.524 |
| AF111160 | Rn\|Glutathione-S-transferase, alpha type (Ya) (Gsta1) | 1.089 | 0.4649 | 6.691 |
| AF169409 | Rn\|solute carrier family 21 (organic anion transporter), member 9 (Slc21a9) | 0.864 | 0.2789 | 5.059 |
| AI170251 | Mm\|18 days embryo whole body cDNA, RIKEN full-length enriched library, clone:1110036H20 | 0.997 | 0.3886 | 6.110 |
| AI228233 | Hs\|epsin 2 (EPN2) | 0.837 | 0.2061 | 3.860 |
| AI716255 | Hs\|cDNA FLJ30167 fis, clone BRACE2000743 | 0.991 | 0.3944 | 6.237 |
| AW914966 | Rn\|5' end/clone=RGIBM90/clone_end=5'/gb=AW914966/gi=8080649/ug=Rn.19878/len=710 | 1.552 | 0.5314 | 5.365 |
| AW915996 | Mm\|RIKEN cDNA A930008K15 gene (A930008K15Rik) | 1.079 | 0.5060 | 7.351 |
| BE114586 | Mm\|10 day old male pancreas cDNA, RIKEN full-length enriched library, clone:1810028E17: cyclin-dependent kinase inhibitor 1A (P21) | 0.873 | 0.5784 | 10.384 |
| BF284065 | Mm\|erythrocyte protein band 4.2 (Epb4.2) | 1.429 | 0.7530 | 8.256 |
| BF284190 | Mm\|similar to thyroid hormone receptor alpha; c-erbAalpha; TR alpha 1 (LOC226107) | 1.413 | 0.4463 | 4.950 |
| BF397229 | Hs\|protocadherin 19 (PCDH19) | 1.233 | 0.3579 | 4.547 |
| BF564460 | Mm\|similar to ATP-binding cassette, sub-family A member 8 (LOC217258) | 1.308 | 0.4097 | 4.910 |
| L31884 | Rn\|tissue inhibitor of metalloproteinase 2 (Timp2) | 1.463 | 0.5467 | 5.855 |
| NM_012532 | Rn\|Ceruloplasmin (ferroxidase) (Cp) | 1.351 | 0.4397 | 5.099 |
| NM_012844 | Rn\|Epoxide hydrolase 1 (microsomal xenobiotic hydrolase) (Epbx1) | 1.459 | 0.4621 | 4.963 |
| U05989 | Rn\|Prostate apoptosis response protein 4 (Pawr) | 0.861 | 0.2510 | 4.568 |

Abbreviations:
Mm(*Mus musculus*), Rn(*Rattus norvegicus*), Hs(*Homo sapiens*)

Validation of Signature: Once the signature had been identified, it was validated using a procedure in which the data was split into 20 different combinations of two thirds and one third, with the two thirds being used to train the signature and one third to test the signature. For scoring purposes, the spleen treatments whose corresponding blood chemistry measurements exhibited a drop in leukocyte counts of 3 fold or greater (versus vehicle-treated control rats) were considered positives and all other spleen treatments were considered negatives. After the 20 iterations were completed, an average set of test values were calculated (shown in Table 3). The statistical calculations were run using SAS version 8 (SAS Institute Inc., Cary, N.C.), using the standard implementations of all methods, except for the log odds ratio, which was calculated as $$\text{Modified log odd ratio} = \ln\frac{(a+0.5)(d+0.5)}{(b+0.5)(c+0.5)}$$

where a=correct negative calls, b=wrong negative calls, c=wrong positive calls and d=correct positive calls.

TABLE 3

Validation Analysis of the Leukocyte Depletion Signature using 20 partitions of a standard data set.

| | |
|---|---|
| Average Correct Negative Call | 49.4 |
| Average Wrong Negative Call | 0.45 |
| Average Wrong Positive Call | 1.2 |
| Average Correct Positive Call | 1.3 |
| Total | 52.35 |
| Chi-Square | 22.86 |
| Probability of Chi-square | 0.242 |
| Continuity-adjusted Chi-Square | 11.27 |
| Probability of Continuity-adjusted Chi-Square | 0.00115 |
| Modified log odds ratio | 4.29 |

Characterization of the Signature: This Signature was then further characterized by comparing it with all the gene expression data in the DrugMatrix™ database to generate a Signature Projection Score (described above). A selection of the results is shown in Table 4.

TABLE 4

Signature Projection Score (SPS) data for selected compounds

| Compounds | Max Bone Marrow Score | Max Spleen Score | Max Fold Serum Leukocyte Depletion |
|---|---|---|---|
| THIOGUANINE # | 24* | 100** | 3.63 |
| DOXORUBICIN # | 41* | 75** | 4.70 |
| METHOTREXATE # | 6 | 75** | 4.35 |
| CHLORAMBUCIL # | 9 | 65* | 7.08 |
| MITOMYCIN C # | 7 | 57* | 3.53 |
| ETOPOSIDE | 43* | 47* | 2.04 |
| LEFLUNOMIDE | 7 | 34* | 2.89 |
| BUSULFAN | 19 | 32* | 0 |
| CARMUSTINE # | 39* | 31* | 4.49 |
| DIETHYLSTILBESTROL | 2 | 30* | No data |
| CISPLATIN | 7 | 25* | 2.01 |
| LOMUSTINE | 3 | 23* | 0 |
| AZATHIOPRINE | 11 | 19 | 0 |
| CYCLOSPORIN A | 2 | 18 | 0 |
| CYTARABINE | 2 | 15 | 2.85 |
| HYDROXYUREA | 13 | 15 | 2.92 |
| IFOSFAMIDE | 79** | 11 | No data |
| CARBOPLATIN | 2 | 8 | 0 |
| ALTRETAMINE | 3 | 5 | 0 |
| BISPHENOL A | 0 | 3 | 0 |
| N,N-DIMETHYLFORMAMIDE | 0 | 3 | No data |
| BITHIONOL | 4 | 2 | 0 |

TABLE 4-continued

Signature Projection Score (SPS) data for selected compounds

| Compounds | Max Bone Marrow Score | Max Spleen Score | Max Fold Serum Leukocyte Depletion |
|---|---|---|---|
| N-NITROSODIETHYLAMINE | 7 | 0 | No data |
| DOXIFLURIDINE | 56* | ND | 0 |
| DAUNORUBICIN | 54* | ND | 2.77 |
| VINORELBINE | 44* | ND | 1.93 |
| OXALIPLATIN | 14 | ND | 2.18 |
| VINBLASTINE | 11 | ND | No data |
| MYCOPHENOLATE MOFETIL | 9 | ND | No data |
| VINCRISTINE | 5 | ND | No data |
| CARBON TETRACHLORIDE | 2 | ND | 0 |
| ETHANOL | 2 | ND | 0 |
| 1-NAPHTHYL ISOTHIOCYANATE | 0 | ND | 0 |

(*= $p < 0.01$, **= $p < 0.001$, # drug used to derived signature - Spleen data only)

The performance of the signature shows preferential matching to the expression data from the compounds used to generate the signature, and also to several other anti-neoplastic or immunosuppressant compounds. Although the signature was derived using spleen expression data, it is apparently valid in bone marrow, as it matches to a similar set of drug treatments in that tissue (see Table 4, above). As would be hoped, the signature matches to expression data derived from animals which suffered a significant drop in blood leukocyte counts (even when the signature algorithm had not included these animals during "training"). For example, see carmustine and etoposide, in Table 4, above.

The signature is comprised of at least two genes involved in the cell cycle and apoptosis, namely GenBank U05989, the rat "prostate apoptosis response protein 4" and GenBank BE114586, which encodes p21 cyclin-dependent kinase inhibitor 1A. Additionally the signature comprises a number of known and unknown cDNAs, whose connection to leukocyte depletion is not obvious from their descriptions at this time.

What is claimed:
1. A method for predicting a biological activity of a test compound, the method comprising:
   a) providing a plurality of drug or group signatures, wherein each said signature is associated with a known biological activity and each said signature comprises a plurality of genes and coefficients indicating the degree of change in expression of said genes in response to one or more compound treatments;
   b) administering a dose of a test compound to a test subject for a selected period of time and obtaining a sample from said test subject;
   c) from said sample determining an expression response $X_g^c$ for each gene g of said plurality of genes $G_s$ in each of said plurality of drug or group signatures; and
   d) calculating the Signature Projection Score (SPS) for each of said plurality of drug or group signatures, wherein

$$SPS(c) = \sum_{g \in G_s} \frac{(X_g^c - R_g)(T_g - R_g)}{S_g},$$

and wherein, $T_g$ is the expression level of gene g of the drug or group signature in response to the one or more compound treatments associated with said drug or group signature, $R_g$ is a reference gene expression level for selected gene g, and $S_g$ is a scaling factor for the contribution of each gene to the SPS, whereby the drug or group signature resulting in the highest SPS indicates the predicted biological activity of the test compound.

2. The method of claim 1, wherein said plurality of drug or group signatures comprises at least 10 signatures.

3. The method of claim 1, wherein said plurality of drug or group signatures comprises at least 25 signatures.

4. The method of claim 1, wherein each of said known biological activity comprises a therapeutic activity.

5. The method of claim 1, wherein each of said known biological activity comprises a toxicological responses.

6. The method of claim 1, wherein each of said known biological activity comprises a therapeutic activity or a toxicological responses.

7. The method of claim 1, wherein said reference gene expression level $R_g$ is expressed as a log ratio and is equal to 0.

8. The method of claim 1, wherein the plurality of drug or group signatures is a plurality of group signatures.

9. The method of claim 1, wherein the plurality of drug or group signatures is a plurality of drug signatures.

10. The method of claim 1, wherein the test subject is selected from the group consisting of an animal, tissue sample, eukaryotic cell, and a prokaryotic organism.

11. The method of claim 1, wherein the test subject is a mammalian cell.

12. The method of claim 1, wherein the test subject is an animal selected from the group consisting of human, monkey, rat, mouse, cow, sheep, dog, cat, chicken, pig, and goat.

13. The method of claim 12, wherein the test subject is a rat.

14. The method of claim 1, wherein said sample is a tissue sample selected from the group consisting of liver, kidney, heart, bone marrow, brain, intestine, and spleen.

15. The method of claim 1, wherein said sample is a liver tissue sample.

16. The method of claim 1, wherein said expression response $X_g$ is determined by measuring the change in expression levels in the sample obtained from the test subject for each gene g using a DNA microarray.

17. The method of claim 1, wherein said plurality of genes of said plurality of drug or group signatures is embodied in a set of polynucleotide probes.

18. The method of claim 17, wherein the set of polynucleotide probes is attached to a substrate in an array.

19. The method of claim 1, wherein said plurality of drug or group signatures is stored in a database on a computer-readable medium.

* * * * *